United States Patent
Schatzmayr et al.

(10) Patent No.: US 8,119,172 B2
(45) Date of Patent: Feb. 21, 2012

(54) MICROORGANISM FOR BIOLOGICAL DETOXIFICATION OF MYCOTOXINS, NAMELY OCHRATOXINS AND/OR ZEARALENONS, AS WELL AS METHOD AND USE THEREOF

(75) Inventors: Gerd Schatzmayr, Vienna (AT); Dian Heidler, Vienna (AT); Elisabeth Fuchs, Vienna (AT); Eva-Maria Binder, Tulln (AT)

(73) Assignee: Erber Aktiengesellschaft, Herzogenburg (AT)

( * ) Notice: Subject to any disclaimer, the term of this patent is extended or adjusted under 35 U.S.C. 154(b) by 62 days.

(21) Appl. No.: 12/155,009

(22) Filed: May 28, 2008

(65) Prior Publication Data

US 2009/0098244 A1 Apr. 16, 2009

Related U.S. Application Data

(63) Continuation of application No. 10/843,305, filed on May 12, 2004, now abandoned, which is a continuation of application No. PCT/AT02/00356, filed on Dec. 19, 2002.

(30) Foreign Application Priority Data

Dec. 20, 2001 (AT) ................ A 2000/2001

(51) Int. Cl.
*A23L 1/28* (2006.01)
*C12N 1/00* (2006.01)

(52) U.S. Cl. ............... 426/60; 426/49; 426/52; 426/62; 435/254.2

(58) Field of Classification Search ............ 426/49, 426/52, 53, 54, 60, 61, 62; 435/252, 254.2, 435/255.1
See application file for complete search history.

(56) References Cited

U.S. PATENT DOCUMENTS

| | | | |
|---|---|---|---|
| 4,004,978 A | 1/1977 | McMullen | 195/51 |
| 5,165,946 A | 11/1992 | Taylor et al. | 426/74 |
| 5,935,623 A | 8/1999 | Alonso-Debolt | 426/2 |
| 6,045,834 A | 4/2000 | Howes et al. | 426/2 |
| 6,096,719 A * | 8/2000 | Matsutani et al. | 514/44 R |
| 6,812,380 B2 * | 11/2004 | Karlovsky et al. | 800/279 |
| 2003/0073239 A1 * | 4/2003 | Karlovsky et al. | 435/468 |

FOREIGN PATENT DOCUMENTS

| | | |
|---|---|---|
| AT | 000504 | 11/1995 |
| AT | 406166 | 7/1999 |
| EP | 0721741 | 7/1996 |
| WO | WO91/13555 | 9/1991 |
| WO | WO92/05706 | 4/1992 |
| WO | WO98/34503 | 8/1998 |
| WO | WO99/57994 | 11/1999 |
| WO | WO00/41806 | 7/2000 |
| WO | WO02/076205 | 10/2002 |

OTHER PUBLICATIONS

Pitout, Biochemical Pharmacology, vol. 18, pp. 485-491, 1969, The Hydrolysis of Ochratoxin a by Some Proteolytic Enzymes.

* cited by examiner

*Primary Examiner* — Leslie Wong
(74) *Attorney, Agent, or Firm* — Jacobson Holman PLLC

(57) ABSTRACT

A microorganism for the biological inactivation or detoxification of mycotoxins, in particular ochratoxins, which is selected from bacteria and/or yeasts, which cleaves the phenylalanine group of the mycotoxins, in particular ochratoxins, as well as a method for biologically inactivating or detoxifying mycotoxins, in particular ochratoxins, in food products and animal feeds by the aid of a microorganism, and the use of the microorganism(s).

15 Claims, No Drawings

US 8,119,172 B2

MICROORGANISM FOR BIOLOGICAL DETOXIFICATION OF MYCOTOXINS, NAMELY OCHRATOXINS AND/OR ZEARALENONS, AS WELL AS METHOD AND USE THEREOF

This application is a Continuation application of U.S. patent application Ser. No. 10/843,305, filed May 12, 2004, now abandoned which is a continuation application of PCT/AT02/00356, filed on Dec. 19, 2002 and published in English.

FIELD OF THE INVENTION

The present invention relates to a microorganism for the biological detoxification of mycotoxins, namely ochratoxins and/or zearalenons, as well as a method for biologically detoxifying mycotoxins, namely ochratoxins and/or zearalenons, in food products and animal feeds by the aid of at least one microorganism, as well as the use of bacteria and/or yeasts to detoxify ochratoxins and/or zearalenons, in food products and animal feeds.

DESCRIPTION OF THE PRIOR ART

Mycotoxins are naturally occurring secondary metabolites of mould fungi affecting agricultural products all over the world and causing toxic effects already in small quantities. The infestation of agricultural products with mycotoxins involves extremely high damage and also induces mycotoxicoses in men and animals, which partially exhibit dramatic effects. Due to the high economic losses and the strain on men and animals caused by mycotoxins and the thus induced mycotoxicoses, attempts have been made for long to find measures to combat mycotoxin contaminations, with basically two methods having been known from the literature. The first approach aims to prevent the growth of mould fungi on food products and animal feeds, thus simultaneously preventing the production of mycotoxins. The second approach is directed at subsequently destroying mycotoxins, or decontaminating food products and/or animal feeds.

Thus, WO 91/13555, for instance, describes a feed supplement as well as a method for inactivating mycotoxins, wherein particles of a phyllosilicate mineral are added to the feed in order to inactivate said mycotoxins. To enhance the effect of these phyllosilicates, the particles are coated with a sequestrant intended to accelerate their actions. Furthermore, an animal feed became known, for instance, from WO 92/05706, which animal feed contains montmorillonit clay as a feed supplement. These natural clay minerals having large internal surface areas are supposed to bind mycotoxins superficially due to their porosity, thus immobilizing the same.

Moreover, a feed supplement is known from Austrian Utility Model AT-U 504, which feed supplement uses an enzyme preparation capable of forming epoxidases and lactonases and chemically degrading mycotoxins both in animal feeds and in the gastrointestinal tract of animals. According to AT-U 504, the activity of this enzyme preparation can be enhanced by the addition of zeolithes and the like.

The addition of mycotoxin binders to animal feeds, which bind to mycotoxins immediately in the digestive tract during digestion, are able to minimize the effects of toxins in livestock. Beside the above-mentioned options, applied substances include alfalfa, bentonite, zeolithe, clays, active carbon, hydrogenated sodium calcium aluminum silicates, phyllosilicates and yeast or bacterium cell walls (U.S. Pat. No. 5,165,946; WO 99/57994; U.S. Pat. No. 6,045,834; EP 9721741; U.S. Pat. No. 5,165,946; U.S. Pat. No. 5,935,623; WO 98/34503; WO 00/41806). The binding of toxins to such materials is a function of the structural characteristics of the toxins. Thus, no effective mycotoxin binder has so far been found for trichothecenes. A further disadvantage of mycotoxin binders is that they are able to adsorb from the feeds in addition to said toxins also important nutrients like vitamins or antibiotics.

It has been recently found that mycotoxins can be degraded and hence partially detoxified, by microorganisms. An example of the detoxification of mycotoxins and, in particular, trichothecenes is contained in AT-B 406 166, in which a special pure culture of a microorganism belonging to the genus *Eubacterium* and deposited under number DSM 11798 as well as a mixed culture of the genus *Eubacterium* with an *Enterococcus*, which was deposited under number 11799, detoxify trichothecenes by cleaving the epoxy ring present on trichothecenes.

The detoxification of ochratoxins by enzymatic hydrolysis has already been described by M. J. Pitout: The hydrolysis of ochratoxin A by some proteolytic enzymes, Biochem. Pharmacol. 18, 485-491 (1969).

SUMMARY OF THE INVENTION

The present invention aims to provide special microorganisms as well as mixed or pure cultures and also combinations thereof, which are able to biochemically degrade mycotoxins, namely ochratoxins and/or zearalenons, in a selective manner and convert the same into physiologically safe substances and, in particular, safe substances for the feeds and food industries.

To solve these objects, the microorganism according to the invention, of the initially defined kind is essentially characterized in that a microorganism and, in particular, aerobic or anaerobic detoxifying bacteria or yeasts is/are used, which cleave(s) the phenylalanine group of the ochratoxins and degrade zearalenons, respectively, wherein the mycotoxin-detoxifying bacteria are selected from the species *Sphingomonas, Stenotrophomonas, Ochrabactrum, Ralstonia* and/or *Eubacterium*, and/or the detoxifying yeasts are selected from the species *Trichosporon, Cryptococcus* and/or *Rhodotorula*. By using a microorganism and, in particular, aerobic or anaerobic detoxifying bacteria or yeasts which cleave the phenylalanine group of the ochratoxins and degrade zearalenons, respectively, it is feasible to convert ochratoxins and, in particular, ochratoxin A or ochratoxin B into those metabolites which have no phenylalanine group and, therefore, do no longer exhibit the toxic effects of ochratoxins. This metabolization of ochratoxins is effected by an enzyme similar to carboxypeptidase A, which cleaves the amide bond of the ochratoxin directly or via a multi-enzyme complex by which the ring of the phenylalanine is hydroxylated and subsequently cleaved and degraded. Finally, the remaining aspartame is cleaved, thus yielding another nontoxic ochratoxin metabolite. This route can be demonstrated in a simple manner:

By using the microorganisms according to the invention, which are selected from bacteria and/or yeasts, it is feasible to detoxify not only ochratoxin A and ochratoxin B, but also the metabolites 4R-hyroxyochratoxin A, 4S-hydroxyochratoxin A, ochratoxin C, ochratoxin A methyl ester, ochratoxin B methyl ester and ochratoxin B ethyl ester. Furthermore, these microorganisms enable the degradation and hence detoxification of zearalenons.

The fact that, according to the present invention, both aerobic and anaerobic detoxifying bacteria, or yeasts can be used as microorganisms is of particular relevance, since, in the event of the intake of food products and/or animal feeds contaminated with the respective microorganisms, detoxification can be achieved even after the intake of such food products and/or animal feeds. This detoxification may occur at any stage, or in any phase, of the passage of the foodstuff or feed within the gastrointestinal tract, because the respective microorganisms or combinations thereof can be selectively caused to enter into effect in each case. The conditions within the gastrointestinal tract from the stomach to the colon are known to be increasingly anaerobic, which means that the redox potential is increasingly reduced such that, upon ingestion of a foodstuff and/or feeds contaminated with the respective mycotoxins or ochratoxins and/or zearalenons, detoxification at first can be started with aerobic bacteria and/or yeasts and continued with the respective anaerobic bacteria and/or yeasts at the end of a digestive process, or if the foodstuff or feed has already reached an intestinal segment where anaerobic conditions prevail.

A particularly complete detoxification of mycotoxins, namely ochratoxins and/or zearalenons, is feasible if detoxifying bacteria selected from the species *Sphingomonas, Stenotrophomonas, Ochrobactrum, Ralstonia* and/or *Eubacterium*, and/or detoxifying yeasts selected from the species *Trichosporon, Cryptococcus* and/or *Rhodotorula* are used as said microorganisms. Among these completely detoxifying bacteria and/or yeasts, the detoxifying bacteria selected from *Sphingomonas* sp. DSM 14170 and DSM 14167, *Stenotrophomonas nitritreducens* DSM 14168, *Stenotrophomonas* sp. DSM 14169, *Ralstonia eutropha* DSM 14171 and *Eubacterium* sp. DSM 14197, as well as the detoxifying yeasts selected from *Trichosporon* spec. nov. DSM 14153, *Cryptococcus* sp. DSM 14154, *Rhodotorula yarrowii* DSM 14155, *Trichosporon mucoides* DSM 14156 and *Trichosporon dulcitum* DSM 14162 have proved to be particularly efficient, since they not only ensure the complete degradation of mycotoxins, but can additionally be safely used in food products and animal feeds, which is not necessarily the case with a plurality of other mycotoxin-cleaving and/or degrading bacteria and yeasts.

Among said further bacteria or yeasts that are likewise capable of degrading microorganisms, those indicated below can be successfully applied, being usable either in a medium or in a buffer, or effective in both substances.

| Strain | Origin | Degradation in medium | Degradation in buffer |
| --- | --- | --- | --- |
| Pseudomonas cepacia | soil | 60% | 100% |
| Ochrobactrum | soil/water | 100% | 100% |
| Achromobacter | soil/water | 50% | 100% |
| Ralstonia | soil/water | 100% | 100% |
| Stenotrophomonas | soil/water | 100% | 100% |
| Rhodococcus erythropolis | DSM 1069 | 75% | 90% |
| Agrobacterium sp. | DSM 30201 | 20-100% | 60-100% |
| Agrobacterium tumefaciens | DSM 9674 | 25-40% | 0-60% |
| Pseudomonas putida | ATCC 700007 | 10-50% | 0% |
| Comomonas acidovorans | ATCC 11299a | 20-57% | 0-50% |
| Ascomyceten yeast | HA 168 | 95% | 40% |
| Cryptococcus flavus | HB 402 | 90% | 100% |
| Rhodotorula mucilaginosa | HB 403 | 20% | 0% |
| Cryptococcus laurentii | HB 404 | 50% | 0% |
| Unknown | HB 508 | 30% | 30% |
| Trichosporon spec. nov. | HB 704 | 40% | 40% |
| Unknown | HB 529 | 100% | 95% |
| Asocomycetes yeast | HA 1265 | 90% | 0% |
| Asocomycetes yeast | HA 1322 | 0% | 95% |
| Trichosporon ovoides | HB 519 | 100% | 90% |
| Triosporon dulcitum | HB 523 | 100% | 100% |
| Rhodotorula fujisanensis | HB 711 | 30% | 0% |
| Cryptococcus curvatus | HB 782 | 20% | 95% |
| Trichosporon guehoae | HB 892 | 50% | 20% |
| Trichosp. coremiiforme | HB 896 | 40% | 20% |
| Trichosporon mucoides | HB 900 | 100% | 100% |
| Trichosporon cutaneum | ATCC 46446 | 0% | 70% |
| Trichosporon dulcitum | ATCC 90777 | 0% | 100% |
| Trichosporon laibachii | ATCC 90778 | 0% | 100% |
| Trichosporon moniliiforme | ATCC 90779 | 0% | 60% |
| Cryptococcus humicolus | ATCC 90770 | 0% | 30% |
| Eubacterium sp. | F6 | 30-70% | 100% |
| Eubacterium callanderi | Di1_8 | 90% | 100% |
| Streptococcus sp. | Dü2_20 | | 40-70% |
| Lactobacillus vitulinus | Ru8 | | 0-100% |
| Stenotrophomonas nitritreducens | DSM 17575 | 100% | 100% |
| Stenotrophomonas nitritreducens | DSM 17576 | 50% | 100% |
| Stenotrophomonas sp. | DSM 13117 | 50% | 95% |

It has proved particularly advantageous, as in correspondence with a preferred further development of this invention, that the bacteria and/or yeasts are stabilized particularly by lyophilization, spray-drying or microencapsulation. By stabilizing said microorganisms, their viability and life-time are improved or enhanced, and, in addition, they will be applicable on a more universal scale, and hence usable at any time in any desired application, in the stabilized state. Stabilization through lyophilization, spray-drying or microencapsulation is known per se, these being simple and rapidly realizable methods that yield stable, viable microorganisms.

According to a further development of the invention, the bacteria or yeasts are used as cell-free extracts or crude extracts. In doing so, a further development in using a cell-free extract contemplates that the latter is used in a solution and, in particular, an aqueous solution. Aqueous solutions of cell-free extracts offer the advantage that, being sprayed on the food or feed to be treated, they get into contact with the contaminating mycotoxins directly on the surfaces of the same, detoxification thus being achieved already immediately upon spraying of said extract. The use of a crude extract of bacteria and yeasts, which is obtained by applying ultrasound, enzymatic digestion, a combination of shock-freezing and thawing, a flow homogenizer, a French press, autolysis at a high NaCl concentration, and/or a bead mill, has the advantage that such a crude extract can be obtained in a particularly quick and unproblematic manner such that, in particular, in those cases where the rapid use of detoxifying or mycotoxin-degrading substances is required, the use of a crude extract yields rapid and reliable results. Moreover, crude extracts can be directly used in the production of animal feed such that the feed supplemented with microorganisms will be taken up by the animals, and the microorganisms and, in particular, yeasts or bacteria will enter into action only in the digestive tract of the animal. In this context, the invention also contemplates the use of a mixture containing the crude extracts of various detoxifying bacteria and/or yeasts.

The use of microorganisms in an unbuffered or buffered solution containing phosphate or trishydrochloride buffer at a pH value of between 1 and 12 and, in particular, 2 and 8, as in correspondence with a preferred embodiment, offers the advantage that the microorganisms can be administered directly with the foodstuff or feeds, thus entering into action in the gastrointestinal tract in those regions where the redox potential is suitable for the optimum action of the microorganisms employed. The use of a buffered solution renders feasible the immediate adaptation to the respective pH prevailing in the gastrointestinal tract such that the food or delicacy good supplemented with the buffered solution of microorganisms will not cause any shift or disturbance of the pH prevailing in the gastrointestinal tract, thus enhancing the easy digestibility of the supplemented food or feeds on the one hand and preventing any digestive disturbance in the gastrointestinal environment.

Another object of the present invention resides in providing substances or microorganisms which can be used to detoxify food products or delicacy goods without impairing or affecting the living beings ingesting the same and without impairing or affecting said food products or delicacy goods treated therewith, apart from detoxifying the mycotoxins present on said food products or delicacy goods.

To solve these objects, it was found according to the invention that the use of bacteria selected from *Sphingomonas* sp. DSM 14170 and DSM 14167, *Stenotrophomonas nitritreducens* DSM 14168, *Stenotrophomonas* sp. DSM 14169, *Ralstonia eutropha* DSM 14171 and *Eubacterium* sp. DSM 14197, and/or yeasts selected from *Trichosporon* spec. nov. DSM 14153, *Cryptococcus* sp. DSM 14154, *Rhodotorula yarrowii* DSM 14155, *Trichosporon mucoides* DSM 14156 and *Trichosporon dulcitum* DSM 14162 enables the mycotoxins, namely ochratoxins, present on the surfaces of food products or animal feeds to be detoxified by cleaving the phenylalanine group and zearalenons to be cleaved, without affecting or influencing in any manner whatsoever the food products or animal feeds treated therewith.

The use of *Trichosporon* spec. nov. DSM 14153, *Eubacterium* sp. DSM 14197 or *Stenotrophomonas nitritreducens* DSM 14168 has proved particularly suitable for this purpose, those microorganisms ensuring the, in particular, complete degradation of mycotoxins, namely ochratoxins and/or zearalenons, without entailing any risk.

In order to enable the, in particular, economical detoxification of mycotoxins, particularly in food products or animal feeds, mixed cultures or combinations of several bacteria and/or yeasts are used for the detoxification of ochratoxins and/or zearalenons in food products and/or animal feeds.

Another object of the present invention resides in providing a method for biologically detoxifying by a microorganism, mycotoxins, namely ochratoxins and/or zearalenons, in food products and animal feeds, which enables the contaminating toxins to be completely and rapidly decontaminated directly upon entering into contact with food products or animal feeds, or within the digestive tract of the living beings taking in said food products or animal feeds.

To solve these objects, the method according to the invention is essentially characterized in that a microorganism according to the invention and, in particular, bacteria and/or yeasts according to the invention are mixed with the food product or animal feeds in amounts ranging from 0.01% by weight to 1% by weight and, in particular, 0.05% by weight to 0.5% by weight. By mixing in solid form the food product or animal feed with the microorganism according to the invention and, in particular, with the bacteria or yeasts according to the invention, a food product or animal feed supplemented with the accordingly stabilized microorganism will be obtained in stable form. If such a food product or animal feed supplemented with the microorganism according to the invention is taken up, a suspension will form during insalivation, and the detoxification of the food product or animal feeds and, in particular, the degradation of ochratoxins will start immediately upon the intake of said food product or animal feeds by man or animal, respectively. In this manner, the complete degradation of noxious mycotoxins, namely ochratoxins and/or zearalenons, in the gastrointestinal tract of the intaking host animal is ensured such that the organism will not be strained by noxious mycotoxins in any manner whatsoever.

If already detoxified food products or animal feeds are intended to be ingested, a further development of the invention provides for the mixing of said food products or animal feeds by stirring in an aqueous suspension of said microorganism containing water at 20 to 99% by weight and, in particular, 35 to 85% by weight, at temperatures of from 10 to 60° C. and, in particular, 15 to 45° C., for 2 minutes to 12 hours and, in particular, 5 minutes to 2 hours. By treating the food product or animal feeds by stirring in an aqueous suspension of the respective microorganism, it is feasible, on the one hand, to provide an intimate contact with the detoxifying microorganisms, of the food product or animal feeds to be treated and, on the other hand, to provide careful treatment of the microorganisms, thus ensuring that the latter will not be deteriorated or killed when mixed with the food product or animal feed. During mixing it is, above all, important to take care that both that the mixing temperatures will not become too high or too low and the duration and composition of the slurry or suspension will fully comply with the present invention so as to safely prevent the destruction or killing of the microorganisms.

DETAILED DESCRIPTION OF PREFERRED EMBODIMENTS

In the following, the invention will be explained in more detail by way of examples relating to the isolation of the microorganisms and their mode of action.

1. Cultivation, Production and Recovery of the Yeast *Trichosporum* Spec. Nov. (DSM 14153)

The following culture medium is used for growing the yeast:

| | |
|---|---|
| 10 g | yeast extract |
| 20 g | malt extract |
| 10 g | glucose |
| 5 g | peptone |
| 400 ppm | ochratoxin A |
| 1 l | RO water |
| pH | 5.5 |

It is treated for 25 minutes at 121° C. in an autoclave. 30 ml of a pre-culture are prepared in a 100 ml Erlenmeyer flask (inoculation rate 0.33%). Incubation is effected for 72 hours at 25° C. on the shaker. The bacterial count obtained is about $5 \times 10^7$/ml.

These 30 ml subsequently serve the pre-culture as an inoculum for fermentation in a 75 liter fermenter. The following cultivation medium is used for fermentation:

| | |
|---|---|
| Malt extract | 4 g/l |
| Yeast extract | 10 g/l |
| Peptone | 5 g/l |
| Glucose | 10 g/l |
| Antifoaming agent | 0.1% |
| pH | 5.5 |

A $pO_2$ of 40% and a maximum aeration rate of 3 m³/h are adjusted as additional parameters. The pH is 5.00 at the beginning, yet changes in the course of the growth process (rising up to 8.5). After about 40 to 44 hours, the contents can be used as an inoculum for the 3.6 m³ production fermenter. The following medium is used for the latter:

| Malt extract     | 17 g/l |
|------------------|--------|
| Yeast extract    | 5 g/l  |
| Peptone          | 2 g/l  |
| Antifoaming agent| 0.1%   |

The aeration rate is 15 m³ air per hour. After 40 to 48 hours, the cells are concentrated by means of a flow separator. The fermentation broth can be concentrated to about 1:10 by means of a separator with a bacterial count of about $3\times10^9$/ml being obtained.

Subsequent stabilization is effected by freeze-drying or spray-drying. Whey powder serves as a cryoprotector in freeze-drying.

10% is added, based on the concentrate volume. After this, the concentrate is frozen at −80° C. Freeze-drying is carried out at a pressure of 0.400 mbar, at a shelf area temperature of 20° C. The duration at a layer thickness of 1.5 cm is about 30 hours.

Spray-Drying Parameters:
    Entry temperature of drying medium (air): 160° C.
    Exit temperature: 80° C.
    Pressure: 3 bar 2. Cultivation, Production and Recovery of the Bacterium *Stenotrophomonas nitritreducens* (DSM 14168)

The cultivation of this bacterium takes place in a nutrient broth, once in Oxoid CM 001 B and once in CM 067 B with 400 ppb ochratoxin A. 30 ml of the medium are autoclaved in a 100-ml Erlenmeyer flask for 25 minutes at 121° C. 1.5 ml from a working cell bank tube serves as an inoculum. Incubation takes place at 30° C. for 72 hours on the shaker.

These 30 ml subsequently serve the pre-culture as an inoculum for fermentation in a 75-liter fermenter. The following cultivation medium is used for fermentation:

| Peptone from meat | 5 g/l |
|-------------------|-------|
| Meat extract      | 3 g/l |
| Antifoaming agent | 0.1%  |

A $pO_2$ of 40% and a maximum gassing rate of 3 m³/h are adjusted as additional parameters. The stirring rate is 200 rpm. The pH is about 6.8 to 6.9 at the beginning, yet changes in the course of the growth process, rising up to 8.3. After about 40 to 44 hours, the contents can be used as an inoculum for the 3.6 m³ production fermenter. The following medium was used for the latter:

| Soybean flour     | 17 g/l |
|-------------------|--------|
| Yeast extract     | 5 g/l  |
| Peptone           | 2 g/l  |
| Antifoaming agent | 0.1%   |

The aeration rate is adjusted to 15 m³ air per hour. The stirring speed is 250 rpm.

After 40 to 48 hours, the cells can be concentrated by means of a flow separator. The concentration ratio is about 1:100.

Subsequent stabilization is effected by freeze-drying or spray-drying. Whey powder serves as a cryoprotector in freeze-drying.

10% is added in most cases, based on the concentrate volume. After this, the concentrate is frozen at −80° C. (10 h) or by the aid of liquid nitrogen (2 h). Freeze-drying is effected at a pressure of 0.400 mbar, at a shelf area temperature of 20° C. The duration at a layer thickness of 1.5 cm is about 30 hours.

Spray-Drying Parameters:
    Entry temperature of drying medium (air): 160° C.
    Exit temperature: 80° C.—
    Pressure: 3 bar 3. Cultivation, Production and Recovery of the Bacterium *Eubacterium* sp. (DSM 14197)

The following medium is used to cultivate this anaerobic bacterium:

| D(+)-glucose                                                                                                                              | 4 g/l    |
|-------------------------------------------------------------------------------------------------------------------------------------------|----------|
| Peptone from casein                                                                                                                       | 2 g/l    |
| Yeast extract                                                                                                                             | 2 g/l    |
| Mineral solution I                                                                                                                        | 75 ml/l  |
| [$KH_2PO_4$ 6 g/l]                                                                                                                        |          |
| Mineral solution II                                                                                                                       | 75 ml/l  |
| [$K_2HPO_4$ 6 g/l; $(NH_4)SO_4$ 6 g/l; NaCl 12 g/l; $MgSO_4 \times 7H_2O$ 2.5 g/l; $CaCl_2 \times 2\, H_2O$ 3 g/l]                          |          |
| Hemin                                                                                                                                     | 1 mg/l   |
| Fatty acid mixture                                                                                                                        | 3.1 ml/l |
| Cystein-HCl                                                                                                                               | 0.5 g/l  |
| Resazurin                                                                                                                                 | 1 mg/l   |
| Ochratoxin A                                                                                                                              | 400 ppb  |
| pH                                                                                                                                        | 6.9      |

Cultivation takes place in a 100 ml Pyrex flask with a silicone septum. 80 ml of the autoclaved medium are decanted and mixed with $KH_2PO_4/Na_2HPO_4$ buffer (pH 7). After the addition of the contents of a cryovial from the working cell bank, the headspace of the flask is gassed with $N_2$ (1 min). Upon closure of the vial, the latter is incubated at 37° C. for 72 hours.

After this, 4.5 liters of the above-mentioned culture solution are autoclaved in a 5-liter Schott flask. The latter comprises a bleeder connection and two tubes with sterile filters (for gassing the inoculum). After cooling of the medium to 37° C., the buffer solution (1% of the phosphate buffer) and subsequently 80 ml inoculum are added. After gassing of the headspace with nitrogen (for 5 min), the openings are closed by means of tube clamps and the inoculum is incubated at 37° C. for about 64 hours. After a purity test, it can be used as an inoculum for a 1 m³ fermenter (700 liter capacity).

The following medium is used for production:

| Glucose       | 10 g/l  |
|---------------|---------|
| Yeast extract | 5 g/l   |
| Peptone       | 2 g/l   |
| Cystein HCl   | 0.5 g/l |
| pH            | 7.00    |

The inoculum is added after the sterilization of the medium in a fermentation tank (40 min, 121° C., 1.21 bar) and recooling to 37° C. The headspace of the fermenter is flushed with $N_2$. The stirring rate is 100 rpm, soda lye (8 mol/l) is used for pH adjustment. The redox potential is about −240 mV at the beginning, decreasing to more than −500 mV during growth.

The fermentation time is about 48 hours. Concentration is effected by means of a flow separator.

Subsequent stabilization is effected by freeze-drying, microencapsulation or spray-drying. Whey powder serves as a cryoprotector in freeze-drying.

10% is added, based on the concentrate volume. After this, the concentrate is frozen at −80° C. (10 h) or by the aid of liquid nitrogen (2 h). Freeze-drying is effected at a pressure of 0.400 mbar, at a shelf area temperature of 20° C. The duration at a layer thickness of 1.5 cm is about 30 hours.

The microorganism is protected from unfavorable living conditions during storage by fluidized-bed granulation using a vegetable fat (Holtmelt process, top spray).

| | |
|---|---|
| Spraying rate: | ca. 80-150 g/min |
| Temperature of incoming air: | 50° C. |
| Spraying pressure: | 3 bar |
| Air amount: | 750-1500 m³/h |
| Product temperature: | <47° C. |

Spray-Drying Parameters:
  Entry temperature of drying medium (inert gas): 160° C.
  Exit temperature: 80° C.
  Pressure: 3 bar 4. Detoxification of Ochratoxin A (OTA) by the Bacterial and Yeast Products According to Examples 1 to 3

A logarithmic dilution series to stage $10^{-4}$ is prepared in physiological saline solution from the products obtained in Examples 1 to 3. Of stages $10^{-1}$ to $10^{-4}$, 2 ml are each pipetted into 18 ml of the respective medium (minimal medium ($Na_2HPO_4$ 2.44 g/l; $KH_2PO_4$ 1.52 g/l; $(NH_3)_2SO_4$ 0.50 g/l; $MgSO_4 \times 7H_2O$ 0.20 g/l, $CaCl_2 \times 2H_2O$ 0.05 g/l), yeast medium or nutrient broth (Oxoid CM001B)), supplemented with 200 ppb OTA. The used flasks are incubated on a horizontal shaker under suitable conditions. After 2.5, 5 and 24 hours, samples are taken and examined for OTA cleavage by means of high-pressure liquid chromatography. At a dilution stage of $10^{-3}$ (corresponding to product bacterial counts of $10^5$), the yeasts in minimal medium have cleaved 90% of ochratoxin A after 5 hours and 100% after 24 hours.

If the complex yeast medium is used as a test matrix, the products exhibit a cleavage rate of 90% after 6 hours at a dilution stage of $10^{-2}$. After 24 hours, all of the OTA is detoxified.

The bacterial products in minimal medium at a dilution stage of $10^{-3}$ (bacterial count from $10^6$-$10^9$) detoxified 40 to 100% of ochratoxin A after 2.5 hours, and 100% after 24 hours. In nutrient broth, detoxification proceeds somewhat slower—at stage 3, 40 to 50% is detoxified after 2.5 h and 80 to 100% after 24 hours. These tests demonstrate that the microorganisms can be converted into stable products exhibiting detoxification activities both in minimal and in complex media.

5. Ochratoxin Degradation (OTA) by Lyophilisates in Stimulated Intestinal Environment Test Model A This model serves to investigate lyophilisates of the yeast strains DSM 14153, DSM 14154, DSM 15155, DSM 14156 and DSM 14162 as well as the aerobic (DSM 14170, DSM 14167, DSM 14168 und DSM 14169) and anaerobic (DSM 14197) bacterial strains. The small bowel of a freshly slaughtered pig is cut into pieces of about 15 cm length, which are each added to 100 ml minimal medium containing OTA [200 ppb]. The batches were finally inoculated directly with 1 g lyophilisate and incubated at 35° C. After 0, 6, 24 and 48 hours, samples were drawn for a subsequent OTA analysis by means of HPLC and stored in a deep-frozen state (−20° C.) until said analysis.

Among the yeasts, germs DSM 14153, DSM 14156 and DSM 14162 proved to be the most active ones. Already after the first six hours of incubation, 70 to 90%, 50 to 90% and 80 to 90%, respectively, of the present toxin had been transformed (after 24 h: 90 to 95%). The two other tested yeasts (DSM 14154, DSM 14155) lagged behind the three above-mentioned strains in terms of activity (0 to 20% degradation after 6 h; 30 to 50% after 24 h; 80% after 48 h).

Among the aerobic bacteria, germ DSM 14168 was the best; after 6 hours, 50 to 100% of the present toxin had already been reacted, after 24 hours 80 to 100%. DSM 14169 too turned out to be absolutely "acceptable": after 6 hours, 0 to 90% OTA had been detoxified, after 24 hours 70 to 95%. The two remaining germs clearly performed less well (0-40% after 6 h; 50 to 60% after 24 h; 60-80% after 48 h).

The anaerobic small-bowel isolate DSM 14197 degraded the present mycotoxin after 6 hours of incubation at a ratio of 0 to 60%; after 24 hours, between 50 and 100% OTA had been reacted.

Analogous tests were carried out with the following germs:

| | |
|---|---|
| Small bowel isolate F6: | 90-95% after 24 h |
| Colon isolate Di 1-8: | 80-95% after 24 h |
| *Trichosporon ovoides*: | 40-50% after 24 h |
| *Triosporon dulcitum*: | 50-90% after 24 h |
| *Cryptococcus curvatus*: | 40-50% after 24 h |
| *Trichosporon laibachii*: | 50% after 24 h |
| *Stenotrophomonas nitritreducens*: | 60-95% after 24 h |
| *Stenotrophomonas sp.*: | 50-70% after 24 h |

This model demonstrated that OTA could be deactivated by the produced products in buffer medium containing an intestinal section with the appropriate environment (nutrients and intestinal flora).

Test Model B

This model served to examine lyophilisates of the yeast strains DSM 14153, DSM 14156 and DSM 14162 as well as the bacterial strains DSM 14168 (aerobic), DSM 14169 (aerobic) und DSM 14197 (anaerobic).

The small bowel of a freshly slaughtered pig was cut into pieces of about 25 cm length, which were closed on their ends by means of cords. 1 g of the product to be examined was weighed into a 50 ml centrifugal tube and resuspended in 20 ml test medium containing OTA [200 ppb] (aerobic germs and yeasts→minimal medium; anaerobic germs→anaerobic buffer). Departing from the thoroughly blended suspension, also tenfold dilutions were optionally prepared. The mixed suspension(s) were then each injected directly into a bowel piece. After having drawn a zero sample directly from the bowel piece, the latter was incubated at 35° C. suspended in a 250-ml Pyrex bottle (i.e. the cord of one end was fixed by the screw cap of the bottle). After 6, 24 and 48 hours, further samples were drawn for a subsequent OTA transformation analysis by means of HPLC.

In the case of yeasts (about $10^7$ KBU/ml), a degradation of OTA up to 90% (DSM 14153) was recorded after 6 hours. After 24 hours at most, comparably high activities (80 to 100%) could be detected for all of the samples.

Comparable results were obtained also with tenfold and hundredfold dilutions of the lyophilisates. Similar results were obtained with the two aerobic bacteria DSM 14168 and DSM 14169. After 6 hours, 20 to 60% of OTA was transformed, after 24 hours 80 to 95%. The anaerobic germ DSM 14197 showed a degradation performance of between 40 and 50% after 6 hours, which was raised to 90% after 24 hours. Bowel sections incubated with OTA, yet without any products displayed no detoxification activities at all.

These tests showed that ochratoxin-detoxifying microorganisms were able to degrade this toxin also in a bowel-corresponding environment. Thus, the application of the microorganisms as food or feed supplements particularly for the detoxification of ochratoxins was clearly demonstrated.

6. Detoxification of Food Products and Animal Feeds

The ochratoxin-detoxifying microorganisms were cultivated for about 66 hours according to Examples 1 to 3 under the appropriate conditions. 25 ml of the suspension were each centrifuged for 15 min at 3210×g and taken up in an adequate volume of minimal medium supplemented with 200 ppb OTA. The suspension forming was used to inoculate 25 g or 25 ml foodstuff, coffee powder, hominy grits, semolina, beer and wine. After careful blending of the foodstuff with the microorganism suspension, a sample (=zero sample) was drawn. The incubation of the batches took place at 25° C. for 9 days. After this, 5 g of the sample were analyzed in comparison with the zero sample. In addition, blanks were co-incubated. The latter were provided with OTA, yet without microorganisms. To analyze the ochratoxin contained in the liquid foods, precisely 1 ml of each food freed of the microorganisms was acidified with 0.5 ml 1M phosphoric acid and extracted with 5 ml methylene chloride. 5 ml of the extract were dried under nitrogen. Each sample was processed twice, the residue after drying was taken up once in acetonitrile/water/acetic acid (45:54:1) and once in toluene/acetic acid (99:1). The analyses of the samples were carried out both by means of HPLC and by means of TLC. When analyzing the semolina, 5 g of the sample were weighed into a 100 ml Schott flask and shaken for one hour with 20 ml acetonitrile/water (60:40) at 170 rpm. After filtration, this extract was directly analyzed by means of HPLC. The processing of hominy grits and coffee for the OTA analyses was somewhat more cumbersome. In those cases, 5 g of the samples were each weighed into a 100 ml Schott flask and shaken with 20 ml acetonitrile:water (60:40) for one hour. After filtration, 4 ml of the extract were mixed with 44 ml PBS buffer (0.1% Tween 20) and packed on an immunoaffinity column. Subsequently, the HPLC analysis was made. Both the decrease of OTA and the emergence of the metabolite OTα were determined. No OTα could be detected in the coffee and corn samples due to the column purification applied. The following degradation rates could be obtained:

| | OTA-Reduction in percent | | | | |
|---|---|---|---|---|---|
| Strain | Beer | Wine | Corn | Wheat | Coffee |
| DSM 14153 | 100 (+) | 99 (+) | 94 (+) | 100 (+) | ~67 (+) |
| DSM 14154 | 100 (+) | 94 (+) | 50 (+) | 100 (+) | 0 (−) |
| DSM 14155 | 30 (+) | 0 (−) | 99 (+) | 100 (+) | 0? (−) |
| DSM 14156 | 100 (+) | 95 (+) | 96 (+) | 100 (+) | 30 (+) |
| DSM 14162 | 83 (+) | 12 (+) | 100 (+) | 100 (+) | 0 (−) |
| DSM 14170 | 75 (+) | 0 (−) | 0 (−) | 89 (+) | 0 (−) |
| DSM 14167 | 100 (+) | 4 (+) | 39 (+) | ~90 (+) | 0 (−) |
| DSM 14168 | 100 (+) | 0 (−) | 50 (+) | 94 (+) | 0 (−) |
| DSM 14169 | 100 (+) | 0 (−) | 0 (−) | 91 (+) | 0 (−) |
| DSM 14171 | 100 (+) | 0 (−) | 79 (+) | 81 (+) | 0 (−) |

7. Degradation of Mycotoxins

The microorganisms were cultivated for about 66 hours. After this, they were centrifuged (3210×g, 15 min, room temperature) and the pellets obtained were resuspended in minimal medium. To the minimal medium were added 1 ppm desoxynivalenol, 1 ppm fumonisin $B_1$, 1 ppm zearalenon, 200 ppb aflatoxin $B_1$ and 2 ppm citrinin. Before incubating the batches at 30° C., a sample was taken ("zero sample"). The incubation time was 96 hours. The batches were determined in duplicate by examining for the HPLC analysis once the supernatant (after centrifugation) and once the whole batch. For purification, 3 ml of the supernatants and 2 ml of the overall sample, respectively, were packed on 15 g Extrelut material. After 15 minutes, the samples were diluted with 40 ml ethyl acetate. 7 ml of the ethyl acetate were each dried and taken up in the appropriate solvent. The analysis of aflatoxin $B_1$ and fumonisin $B_1$ was carried out after a preceding derivatization.

The samples after 96 hours were examined for the degradation of the respective toxins in comparison with the samples at the beginning. To this end, both the supernatants (separation of the biomass by centrifugation) and the overall samples (with biomass) were analyzed for DON, ZON and $AFB_1$. The results are illustrated in Table 2.

TABLE 2

| Strain | ZON-degradation rate [%] | | $FB_1$-degradation rate [%] | $AFB_1$-degradation rate [%] | | CIT-degradation-rate [%] |
|---|---|---|---|---|---|---|
| | Supernatant | total | Supernatant | Supernatant | total | Supernatant |
| DSM 14170 | 0 | 24 | 0 | 0 | 0 | 100 |
| DSM 14167 | 0 | 28 | 0 | 0 | 10 | 0 |
| DSM 14168 | 0 | 32 | 0 | 0 | 10 | 0 |
| DSM 14169 | 88 | 90 | 0 | 8 | 46 | 0 |
| DSM 14171 | 0 | 43 | 0 | 0 | 24 | 0 |
| DSM 14153 | 100 | 100 | 19 | 20 | 13 | 0 |
| DSM 14154 | 19 | 67 | 22 | 64 | 63 | 0 |
| DSM 14155 | 81 | 100 | 29 | 20 | 38 | 0 |
| DSM 14156 | 100 | 100 | 6 | 0 | 61 | 0 |
| DSM 14162 | 17 | 62 | 8 | 0 | 0 | 0 |

It is clearly apparent from the foregoing assays that some mycotoxins such as zearalenon (ZON), aflatoxin $B_1$ ($AFB_1$), fumonisin $B_1$ ($FB_1$) can partially be degraded extremely well with the microorganisms according to the invention. Citrinin (CIT) could be degraded 100% merely by the bacterium *Sphingomonas* sp. (DSM 14170).

To sum up, it is noted that the microorganisms according to the invention readily enable, in particular, the degradation of ochratoxins in food products and animal feeds and also in intestinal environment, with the degradation of zearalenon, citrinin and the like yet partially yielding good results.

All microorganisms being cited in the present application have been deposited with DSMZ—Deutsche Sammlung von Mikroorganismen and Zellkulturen GmbH, Mascheroder Weg 1b, 38123 Braunschweig, Germany (DE), the recognized IDA under the Budapest Treaty on the International Recognition of the Deposit of Microorganisms for the Purposes of Patent Procedure, on following dates and have been given the following access numbers.

| Access No. | Deposit date |
|---|---|
| DSM 14156 | 08 Mar. 2001 |
| DSM 14155 | 08 Mar. 2001 |
| DSM 14154 | 08 Mar. 2001 |
| DSM 14153 | 08 Mar. 2001 |
| DSM 14197 | 15 Mar. 2001 |

-continued

| Access No. | Deposit date |
|---|---|
| DSM 14171 | 08 Mar. 2001 |
| DSM 14169 | 08 Mar. 2001 |
| DSM 14168 | 08 Mar. 2001 |
| DSM 14167 | 08 Mar. 2001 |
| DSM 14170 | 08 Mar. 2001 |
| DSM 14162 | 08 Mar. 2001 |

The invention claimed is:

1. A microorganism for the biological detoxification of mycotoxins, including ochratoxins or zearalenons, wherein the microorganism comprising detoxifying yeasts *Trichosporon*, which cleave(s) the phenylalanine group of the ochratoxins and degrade zearalenons, respectively.

2. The microorganism according to claim 1, wherein the detoxifying yeasts are selected from the group consisting of: *Trichosporon* spec, nov. DSM 14153, *Trichosporon mucoides* DSM 14156 and *Trichosporon dulcitum* DSM 14162.

3. The microorganism according to claim 1, wherein the detoxifying yeasts are *Trichosporon* spec, nov. DSM 14153.

4. The microorganism according to claim 1, wherein the yeasts are stabilized by lyophilization, spray-drying or microencapsulation.

5. The microorganism according to claim 1, wherein said microorganism is used in a buffered solution containing acetate, citrate, phosphate or trishydrochloride buffer at a pH of between 1 and 12.

6. A method for detoxification of mycotoxins, including ochratoxins or zearalenons, in food products or animal feeds, comprising the step of cleaving the phenylalanine group of ochratoxin or degrading zearalenon by using yeasts selected from the group consisting of: *Trichosporon* spec, nov. DSM 14153, *Trichosporon mucoides* DSM 14156 and *Trichosporon dulcitum* DSM 14162.

7. The method according to claim 6, wherein *Trichosporon* spec, nov. DSM 14153 is used for the detoxification of mycotoxins, including ochratoxins or zearalenons, in food products or animal feeds.

8. The method according to claim 6, wherein mixed cultures of said yeasts are used for the detoxification of mycotoxins, in food products or animal feeds.

9. A method for biologically detoxifying mycotoxins, including ochratoxins or zearalenons, in food products or animal feeds by the aid of a microorganism, wherein a microorganism according to claim 1 is mixed with the food products or animal feeds in amounts ranging from 0.01% by weight to 1% by weight.

10. The method according to claim 9, wherein said food products or animal feeds are treated by stirring in an aqueous suspension of said microorganism containing water at 20 to 99% by weight at temperatures of from 10 to 60° C. for 2 minutes to 12 hours.

11. The microorganism according to claim 5, wherein the pH is from 2 and 8.

12. The method according to claim 9, wherein the microorganism is mixed with the food products or animal feeds in amounts ranging from 0.05% by weight to 0.5% by weight.

13. The method according to claim 10, wherein said microorganism contains water at 35% to 85% by weight.

14. The method according to claim 10, wherein the temperature is from 15° C. to 45° C.

15. The method according to claim 10, wherein the stirring lasts 5 minutes to 2 hours.

* * * * *